(12) United States Patent
Lin et al.

(10) Patent No.: US 8,480,678 B2
(45) Date of Patent: Jul. 9, 2013

(54) BONE CAVITY CREATION AND METHOD WITH MAGNETIC FORCE RETRIEVABLE BEADS

(75) Inventors: Jiin-Huey Chern Lin, Winnetka, IL (US); Chien-Ping Ju, Kansas City, MO (US); Pong-Jeu Lu, Tainan (TW)

(73) Assignee: Joy Medical Devices Corporation (TW)

( * ) Notice: Subject to any disclaimer, the term of this patent is extended or adjusted under 35 U.S.C. 154(b) by 322 days.

(21) Appl. No.: 12/733,545

(22) PCT Filed: Sep. 8, 2008

(86) PCT No.: PCT/US2008/010452
§ 371 (c)(1),
(2), (4) Date: Nov. 18, 2010

(87) PCT Pub. No.: WO2009/035549
PCT Pub. Date: Mar. 19, 2009

(65) Prior Publication Data
US 2011/0093025 A1    Apr. 21, 2011

Related U.S. Application Data

(60) Provisional application No. 60/993,202, filed on Sep. 11, 2007.

(51) Int. Cl.
*A61F 2/46* (2006.01)

(52) U.S. Cl.
USPC .................................................. 606/86 R

(58) Field of Classification Search
USPC ..................... 606/79, 86 R, 92–94; 600/12
See application file for complete search history.

(56) References Cited

U.S. PATENT DOCUMENTS

| | | | |
|---|---|---|---|
| 6,869,445 B1 * | 3/2005 | Johnson | 623/17.11 |
| 2007/0093822 A1 * | 4/2007 | Dutoit et al. | 606/61 |
| 2010/0260780 A1 * | 10/2010 | Levy et al. | 424/172.1 |

* cited by examiner

*Primary Examiner* — Nicholas Woodall
(74) *Attorney, Agent, or Firm* — Bacon & Thomas, PLLC

(57) ABSTRACT

The present invention discloses a method of using beads to create a cavity in a bone, which includes introducing beads into a bone by applying a pressure on said beads, wherein the beads are metallic beads able to be attracted by a magnet; and withdrawing the beads from the bone by magnetic force. Preferably, a pocket is disposed in the bone prior to the introduction of beads, and the introduction and withdraw of the beads are carried out with respect to said pocket.

10 Claims, 4 Drawing Sheets

BONE CAVITY CREATION AND METHOD WITH MAGNETIC FORCE RETRIEVABLE BEADS

CROSS-REFERENCE TO RELATED APPLICATION

This patent application claims the benefit of U.S. Provisional Patent Application No. 60/993,202, filed Sep. 11, 2007.

FIELD OF THE INVENTION

The present invention is related to a technique for creating a cavity in a bone, in which an orthopaedic paste will be delivered and set to act as a medical implant.

BACKGROUND OF THE INVENTION

It is well accepted that bioresorbable orthopedic implants are always the better choice than permanent foreign-body implants, as long as their bioresorption rates, biomechanical properties and variations in biomechanical properties with respect to the resorption processes are appropriately controlled. Among all bioresorbable orthopedic implants, calcium-based implants (calcium phosphate, calcium sulfate, etc), are perhaps the top choice so far. The conventional methods of forming a hardened (set) bone cement in bone cavity involve creating a bone cavity in advance.

Prior-art cavity creation devices having an inflatable and expandable liquid fluid-filled balloon structure have insufficient "lift"—ability to push back compression-fractured bone (e.g., to restore vertebral body height) under certain circumstances due to the "softness" of the balloon.

Prior-art cavity creation devices having an inflatable and expandable balloon-type structure rely on a high pressure liquid fluid to expand a cavity in bone, which increases various high pressure-related risks in clinical procedures.

Prior-art cavity creation devices having a foldable and extendable (expandable) rigid structure have risks of generating stress-concentrated spots and fresh cracks in the readily fractured bone.

Most prior-art rigid-structure cavity creation devices have a hollow structure under expanded/unfolded condition. Once bone chips/fragments are trapped in such devices during unfolding (expanding) and/or folding (collapsing) procedures, such devices have risks of being unable to be retrieved from the treated site, especially through a minimally invasive percutaneous path. Likewise, in case any pieces/components of the rigid-structure devices break off the structure during procedure, these broken-off pieces/components would be very hard to be retrieved, especially through a minimally invasive percutaneous path.

The inventors of the present application in WO 2006/138398 A2 disclose a non-inflated tool for expanding a bone cavity in which an orthopaedic paste is to be implanted comprising a flexible linear filler and a rod with one end thereof connected to one end of the flexible linear filler, so that the flexible linear filler can be pushed by the rod through a tube into a hole of a bone to expand a bone cavity in the bone. The filler may be a wire, band, or chain. Preferably, the chain comprises a series of beads linked one after another or by a string. Despite the ability of this non-inflated tool to effectively create/expand bone cavity, once the linear filler breaks, it would be very hard to retrieve the broken-loose bodies, especially through a minimally invasive percutaneous path. Another risk for the prior-art non-inflated tool is entanglement of the linear filler, which might happen during feeding (expansion) and/or retrieving procedure. When entanglement happens, it would be very hard for the linear filler to be retrieved, especially through a minimally invasive percutaneous path.

For most prior-art rigid-structure cavity creation devices, an easy, accurate, reliably and safe bone-expansion procedure for a fractured bone is always a great challenge. There is a need in developing an easy, accurate, reliably and safe technique for creating a cavity in a bone, in which an orthopaedic paste is to be implanted.

SUMMARY OF THE INVENTION

A primary object of the present invention is to provide a method and device for creating a cavity in a bone (for example, a fractured vertebral body), in which an orthopaedic paste is to be implanted.

A method of using beads to create a cavity in a bone disclosed in the present invention comprises the following steps: a) introducing beads into a bone by applying a pressure on said beads, wherein said beads are metallic beads able to be attracted by a magnet; and b) withdrawing said beads from said bone by magnetic force.

Preferably, said magnetic force is generated by approaching a magnet to said beads.

Preferably, the method of the present invention further comprises disposing a pocket in said bone prior to said introduction of beads in step a), wherein said disposed pocket has an inlet to let said beads into and out off said pocket, wherein said introduction and said withdraw of said beads in steps a) and b) are carried out with respect to said pocket. More preferably, said inlet of said pocket is fixedly connected to or formed at one end of a tube, so that said beads can be introduced into said pocket via said tube. Most preferably, said introduction of beads in step a) comprises inserting said one end of said tube together with said pocket into said bone; feeding said beads into said tube; and pushing said beads inside said tube from another end of said tube.

Preferably, said withdraw of said beads in step b) comprises b1) inserting a magnet into said tube from said another end to approach said beads in said pocket; b2) retreating said magnet to which said beads are attached from said pocket; and b3) repeating said inserting in step b1) and said retreating in step b2) in sequence until all the beads are withdrawn from said pocket.

Preferably, the method of the present invention further comprises c) withdrawing said tube together said pocket from said bone after all the beads being withdrawn from said pocket in step b).

Preferably, said pocket is a flexible bag.

Preferably, said pocket is a balloon.

Preferably, the method of the present invention further comprises deflating said pocket by sucking off air in said pocket from said another end of said tube before inserting said one end of said tube together with said pocket into said, bone.

Alternatively, said introduction of beads in step a) comprises inserting one end of a tube into said bone; feeding said beads into said tube; and pushing said beads inside said tube from another end of said tube.

Preferably, said withdraw of said beads in step b) comprises b1) inserting a magnet into said tube from said another end to approach said beads in said bone; b2) retreating said magnet to which said beads are attached from said bone; and b3) repeating said inserting in step b1) and said retreating in step b2) in sequence until all the beads are withdrawn from said bone.

Preferably, the method of the present invention further comprises c) withdrawing said tube from said bone after all the beads being withdrawn from said bone in step b).

The present invention also discloses a device for creating a cavity in a bone comprising a needle conduit; a connector; a reservoir; beads in said reservoir, wherein said beads are metallic beads able to be attracted by a magnet; a driver having a piston, wherein a proximal end of said needle conduit is connected to said driver with said connector, said reservoir is in fluid communication with said driver so that said beads flow into said driver, and said piston is able to be driven by an operator to push said beads flown into said driver into said needle conduit and said piston is able to be pulled away from said needle conduit after said pushing to let said beads from said reservoir into said driver.

Preferably, the device of the present invention further comprises a press member in contact with the beads in said reservoir, which presses the beads in the reservoir to enter the driver, so that a space created in the driver is eliminated when the piston is being pulled away from said needle conduit.

Preferably, said driver and said reservoir form a three-way structure, and said reservoir is located between two ends of the three-way structure, wherein said needle conduit and said piston are located at said two ends of the three-way structure. More preferably, said piston is linearly movable in said three-way structure.

The device of the present invention further comprises a pocket fixedly connected to or formed at a distal end of said needle conduit.

Preferably, said driver comprises a cylindrical reservoir base having a longitudinal channel therein and a longitudinal slit which is in fluid communication and aligned with the longitudinal channel; a piston base in which the piston is movably received, wherein said reservoir is intimately received in said longitudinal slit so that said beads in said reservoir flow into the longitudinal channel of the reservoir base without leaking; said proximal end of said needle conduit is connected to a distal end of the reservoir base with said needle conduit being in fluid communication and aligned with the longitudinal channel of the reservoir base; and a distal end of said piston base is connected to a proximal end of the reservoir base with the piston being aligned with the longitudinal channel of the reservoir base, so that the piston can advance and retreat in the longitudinal channel of the reservoir base and in the needle conduit.

Preferably, said piston comprises a rod portion and a threaded portion, wherein said rod portion advances and retreats in the longitudinal channel of the reservoir base and the needle conduit while the threaded portion is threadedly engaged with a proximal end of the piston base.

Preferably, the device of the present invention further comprises a magnetic rod having a magnet at one end, which is adapted to be inserted into the needle conduit with its magnet approaching said pocket.

DETAILED DESCRIPTION OF THE INVENTION

Figure 1:
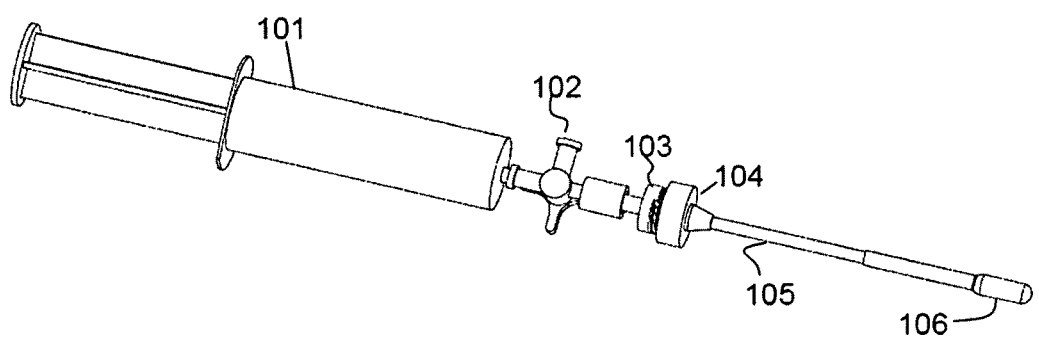
FIG. 1 is a schematic perspective view showing a balloon deflation tool used in the present invention.

The present invention discloses a method for creating a cavity in a bone comprising (a) preparing filler particles capable of being retrieved from said cavity by a retrieving means, therein said retrieving means is capable of magnetically interacting with said filler particles; (b) inserting said filler particles into said bone by a feeding means to expand the bone to a desired volume; and (c) magnetically retrieving the filler particles from the expanded bone by said retrieving means.

The method of the present invention further comprises, prior to inserting the filler particles into the bone, inserting (preferably through a minimally invasively percutaneous path) a delivery tube into the bone; inserting said filler particles into said bone through said tube by said feeding means; and, after the bone is expanded to a desired volume, magnetically retrieving the filler particles from the expanded bone through the delivery tube by the retrieving mean.

The method of the present invention further comprises, prior to inserting the filler particles into the bone, inserting (preferably through a minimally invasively percutaneous path) a balloon into the bone; inserting said filler particles into said balloon by the feeding means to expand the balloon (or the bone) to a desired volume; magnetically retrieving the filler particles from the expanded balloon by the retrieving means; and retrieving the balloon from the expanded bone.

Preferably, a method for creating a cavity in a bone according to the present invention comprises (a) preparing filler particles capable of being retrieved from said cavity by a retrieving means, therein said retrieving means is capable of attracting said filler particles by a magnetic force; (b) preparing a minimally invasive percutaneous path into said bone; (c) inserting a balloon into the bone through said path; (d) inserting said filler particles into said balloon by a feeding means to expand the balloon (or the bone) to a desired volume; (e) magnetically retrieving the filler particles from the expanded balloon by said retrieving means; and (f) retrieving the balloon from the expanded bone.

The feeding means is preferably (not limited to) a plunger capable of being inserted into and retrieved from the bone (preferably through a minimally invasive percutaneous path).

The retrieving means is preferably (not limited to) a plunger capable of being inserted into and retrieved from the bone (preferably through a minimally invasive percutaneous path), therein at least a portion of said retrieving means (preferably the distal portion) being magnetic or capable of being magnetized to be able to attract the filler particles by a magnetic force.

The retrieving means is a hard (permanent) magnet or soft magnet (capable of being magnetized and de-magnetized), or comprises at least a portion in said means a hard magnet or a soft magnet.

Said portion of said retrieving means being magnetic or capable of being magnetized to be able to attract the filler particles by a magnetic force is made from a magnetic material comprising (not limited to) Fe, Co and/or Ni-based alloys, Sm—Fe, Sm—Co and Sm—Co—Fe based alloys, Al—Ni—Co and Al—Ni—Fe—Co based alloys, Nd—Fe—B based alloys, Y—Co based alloys, $Fe_2O_3$, $Fe_3O_4$, $BaO—Fe_2O_3$ and $SrO—Fe_2O_3$ based ceramics.

The feeding means and retrieving means can be solid, porous or hollow, and can be rigid, semi-rigid or flexible.

The balloon is preferably connected to a distal end of said delivery tube, thereby the balloon may be carried into the bone by said tube, wherein the filler particles may be inserted into the balloon through the delivery tube.

The balloon is preferably made from an inflatable, preferably inflatable and expandable, polymeric material (e.g., PU or rubber), although any material in any form which may serve the purpose may be used.

The balloon may be impenetrable to air, penetrable to air, or penetrable to liquid. For air-impenetrable balloon, the delivery tube connected to the balloon may optionally incorporate on the inner wall of said tube at least a groove to help expel the air trapped within the balloon during inserting the filler particles into the balloon.

The filler particles can be made from any material capable of being magnetically attracted by the retrieving means, for example, a Fe, Co and/or Ni based alloy.

The filler particles are preferably in a granular form and have particle sizes smaller than about 3 mm, preferably smaller than about 2 mm, and more preferably smaller than 1 mm. (The particle size should not be too small to avoid embolism complication in case the balloon breaks inside bone).

The filler particles can be solid, porous or hollow, and can be rigid or semi-rigid. For the sake of reducing particle weight (to make the magnetic retrieving process easier) and increasing the "lift" (the ability to push back compression-fractured bone), the filler particles are preferably rigid and hollow, as long as the strength of said hollow particles is sufficient to withstand the loading without being damaged or crushed during expansion process.

The filler particles can be of any shape, but should avoid having sharp edges or corners which more easily damage the balloon. In general, particles of a spherical shape are easier to "flow," thereby increasing the "penetrating" ability of the particles (and the balloon). Particles of a square shape can develop a higher binding strength among particles (due to the larger particle-particle contact area) when the retrieving means is magnetically interacting with (attracting) the filler particles during retrieving procedure. This higher binding strength largely helps the retrieval of the filler particles from the expanded balloon. Combination of these two features (properties) is preferred.

Preferably the filler particles are in a generally spherical shape with at least a portion of the particle surface being substantially flat. More preferably the filler particles are in a generally spherical shape with two portions on opposite sides (ends) being substantially flat. This shape of particles not only enhances the binding strength among particles, but also help direct (align) the filler particles into the delivery tube during retrieving procedure.

A small amount of lubricant (e.g., water or oil) may be optionally added in the balloon or directly onto filler particles to lubricate the particles and help the filler "flow" within the balloon during feeding and/or retrieving procedures.

The method of the present invention may further comprises inserting a bone filler material into said cavity, therein said bone filler is preferably a biocompatible material, and more preferably a biocompatible and bioresorbable material, for example, calcium-based cement or particles or their composites.

The bone being treated can be any kind of bone being damaged, fractured or diseased, for example, a compression-fractured vertebral body.

A three-step process for creating a cavity in a bone, e.g. expanding a collapsed bone, according to one of the preferred embodiments of the present invention will be described in associated with devices constructed according to the present invention shown in the accompanied drawings.

Step 1: Balloon Deflation for Implant

As shown in FIG. 1, a balloon 106 is fixedly mounted to a distal end of a needle conduit 105. The balloon 106 is made of elastic polyurethane or another suitable elastic material. A syringe 101 is used to suck off the air contained in the balloon 106, wherein a proximal end of the needle conduit 105 is connected to a suction conduit 103 with a connector 104, and the suction conduit 103 is then connected to the syringe 101 with a three-way valve 102 being turned on. Once the balloon 106 is deflated, the three-way valve 102 is turned off. The needle conduit 105 together with the deflated balloon 106 are ready to be inserted into a bone (not shown in the drawings) through a minimally invasive percutaneous path (not shown in the drawings). The suction conduit 103 is disconnected from the connector 104 when the balloon 106 is inside the bone.

Step 2: Create Cavity by Embedding Beads

Figure 2:
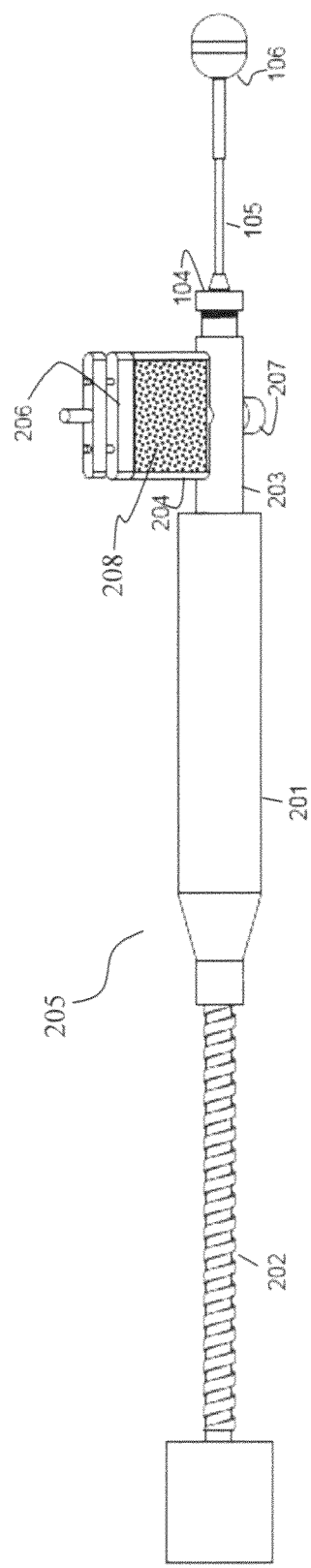
FIG. 2 is a schematic plan view showing a bead-feeding tool for creating a cavity in a bone of the present invention.
Figure 3:
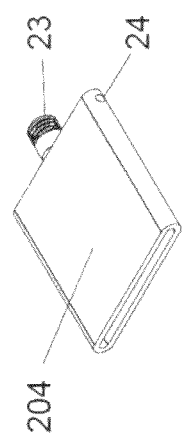
FIG. 3 is a schematic perspective view showing the cartridge 204 used in the bead-feeding tool shown in FIG. 2, which is for storing and supplying beads 208.
Figure 4:
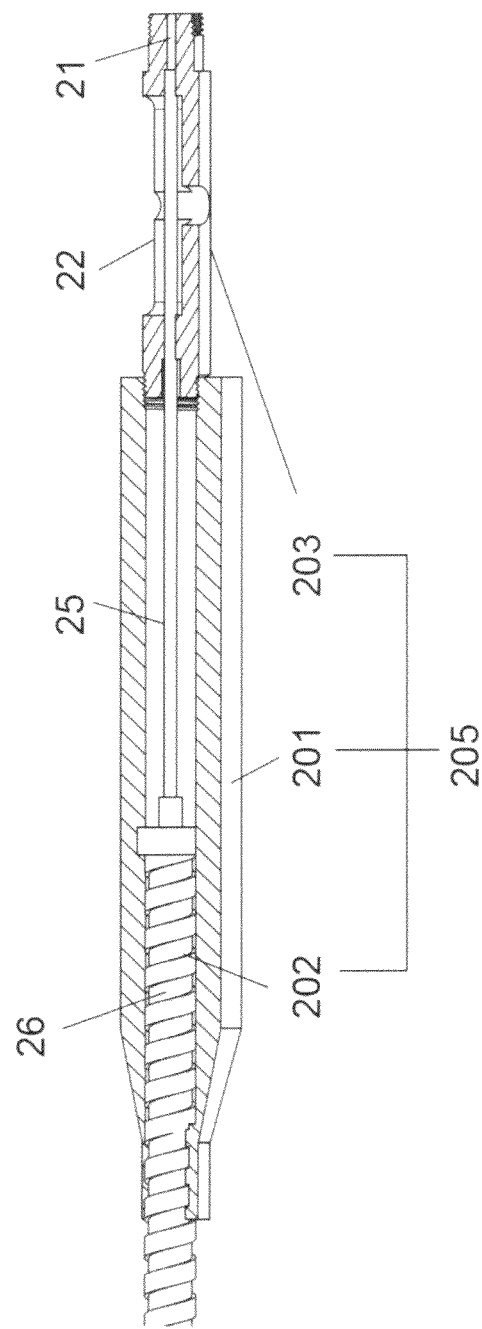
FIG. 4 is a schematic partial cross-sectional view showing the driver 205 used in the bead-feeding tool shown in FIG. 2.

A feeding tool is assembled for filling the balloon 106 with metallic beads made of Fe, Co or Ni based alloy. As shown in FIGS. 2 to 4, the feeding tool comprises a cartridge 204; beads 208 in said cartridge 204; and a driver 205. The driver 205 has a cylindrical cartridge base 203 provided with a longitudinal channel 21 therein and a longitudinal slit 22 which is in fluid communication and aligned with the longitudinal channel 21; a piston base 201; and a piston 202 movably received in said piston base 201. The cartridge 204 has a threaded stud 23 formed on a bottom surface thereof and two opposite through holes 24 on the front and rear sides (only one through hole 24 is shown in FIG. 3) inear the bottom surface. The cartridge 204 is intimately received in said longitudinal slit 22 and the through holes 24 are aligned with the longitudinal channel 21, so that the beads 208 in said cartridge 204 flow into the longitudinal channel 21 without leaking. A nut 207 is threaded into the threaded stud 23 to fix the cartridge 204 onto the cartridge base 203. The piston 202 has a rod portion 25 and a threaded portion 26, wherein the threaded portion 26 is threadedly engaged with a proximal end of the piston base 201. A distal end of said piston base 201 is connected to a proximal end of the cartridge base 203 with the rod portion 25 of the piston being aligned with the longitudinal channel 21 of the cartridge base, thereby said rod portion 25 can advance and retreat in the longitudinal channel 21 and the cartridge 204 when the threaded portion 26 is clockwise and counter-clockwise rotated relatively to the piston base 201. The assembly of the feeding tool is now completed, and it is then connected to the needle conduit 105 by connecting a distal end of the cartridge base 203 to the connector 204.

The piston 202 is able to be driven by an operator to push said beads 208 flown into said driver 205 into said needle conduit 105 and finally into said balloon 106, wherein a distal end of the rod portion 25 travels through the cartridge 204 and the longitudinal channel 21 separated by the cartridge 204 and reaches the balloon 106. Said piston 202 is then driven backward from said balloon 106, passing the needle conduit 105, the longitudinal channel 21, and the cartridge 204, to let said beads 208 in said cartridge 204 flow into said driver 205 (the longitudinal channel 21) again. A pressing member 206 is slidably received in the cartridge 204, pressing the beads 208 therein, to eliminate a space created in the needle conduit 105 and the driver 205, when the piston 202 is being driven away from said balloon 106. The balloon 106 will be dilated with the beads 208 to a predetermined size (i.e. predetermined amount of beads) by repeatedly driving the piston 202 back-and-forth. The feeding tool is then separated from the connector 104.

Step 3: Pull Out Beads by Magnetic Rod

Figure 5:
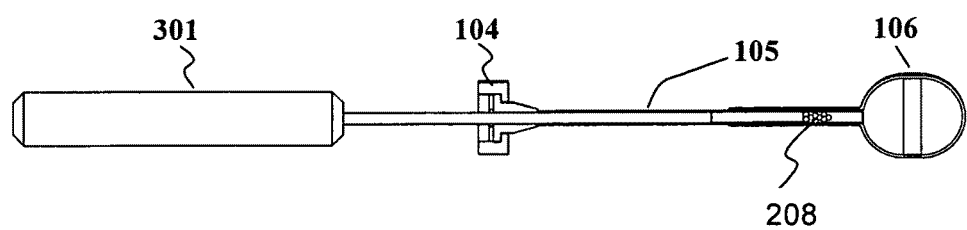
FIG. 5 is a schematic partial cross-sectional view showing that the beads 208 inside the balloon 106 are withdrawn by inserting a magnetic rod 301 into the needle conduit 105.

The beads 208 inside the balloon 106 are withdrawn by inserting a magnetic rod 301 into the needle conduit 105 as shown in FIG. 5. The magnetic rod 301 is provided with a permanent magnet at its front end, and the beads 208 in the balloon 106 are attracted by and attached to the approaching permanent magnet. The magnetic rod 301 is then pulled out from the needle conduit 105 to retrieve the beads attached to its front end. The balloon 106 is removed from the bone cavity by pulling out the connector 104 together with the needle conduit 105, when all the beads 208 inside the balloon 106 have been withdrawn by repeatedly inserting and pulling the magnetic rod 301 in and out the balloon 106. Optionally, Step 1 may be carried out to deflate the balloon 106 prior to pulling out the balloon 106 from the bone cavity.

Although the present invention has been described with reference to specific details of certain embodiments thereof, it is not intended that such details should be regarded as limitations upon the scope of the present invention. Many modifications and variations are possible in light of the above disclosure.

The invention claimed is:

1. A method of using beads to create a cavity in a bone comprising the following steps: a) introducing beads into a bone by applying a pressure on said beads, wherein said beads are metallic beads able to be attracted by a magnet; and b) withdrawing said beads from said bone by magnetic force, wherein said introduction of beads in step a) comprises inserting one end of a tube into said bone; feeding said beads into said tube; and pushing said beads inside said tube from another end of said tube; and said withdraw of said beads in step b) comprises b1) inserting a magnet into said tube from said another end to approach said beads in said bone; b2) retreating said magnet to which said beads are attached from said bone; and b3) repeating said inserting in step b1) and said retreating in step b2) in sequence until all the beads are withdrawn from said bone.

2. The method of claim 1 further comprising disposing a pocket in said bone prior to said introduction of beads in step a), wherein said disposed pocket has an inlet to let said beads into and out off said pocket, wherein said introduction and said withdraw of said beads in steps a) and b) are carried out with respect to said pocket.

3. The method of claim 2 wherein said inlet of said pocket is fixedly connected to or formed at said one end of said tube, so that said beads can be introduced into said pocket via said tube.

4. The method of claim 3 wherein said introduction of beads in step a) comprises inserting said one end of said tube together with said pocket into said bone.

5. The method of claim 4, wherein step b1) comprises inserting a magnet into said tube from said another end to approach said beads in said pocket; step b2) comprises retreating said magnet to which said beads are attached from said pocket; and step b3) comprises repeating said inserting in step b1) and said retreating in step b2) in sequence until all the beads are withdrawn from said pocket.

6. The method of claim 4, wherein said pocket is a flexible bag.

7. The method of claim 4, wherein said pocket is a balloon.

8. The method of claim 1 further comprising c) withdrawing said tube from said bone after all the beads being withdrawn from said bone in step b).

9. A method of using beads to create a cavity in a bone comprising the following steps: a) introducing beads into a bone by applying a pressure on said beads, wherein said beads are metallic beads able to be attracted by a magnet; and b) withdrawing said beads from said bone by magnetic force, and further comprising disposing a pocket in said bone prior to said introduction of beads in step a), wherein said disposed pocket has an inlet to let said beads into and out off said pocket, and said inlet of said pocket is fixedly connected to or formed at one end of a tube, wherein said introduction of beads in step a) comprises inserting said one end of said tube together with said pocket into said bone; feeding said beads into said tube; and pushing said beads inside said tube from another end of said tube; said method further comprising c) withdrawing said tube together said pocket from said bone after all the beads being withdrawn from said pocket in step b).

10. A method of using beads to create a cavity in a bone comprising the following steps: a) introducing beads into a bone by applying a pressure on said beads, wherein said beads are metallic beads able to be attracted by a magnet; and b) withdrawing said beads from said bone by magnetic force, and further comprising disposing a pocket in said bone prior to said introduction of beads in step a), wherein said disposed pocket has an inlet to let said beads into and out of said pocket, and said inlet of said pocket is fixedly connected to or formed at one end of a tube, wherein said introduction of beads in step a) comprises inserting said one end of said tube together with said pocket into said bone; feeding said beads into said tube; and pushing said beads inside said tube from another end of said tube;

said method further comprising deflating said pocket by sucking off air in said pocket from said another end of said tube before inserting said one end of said tube together with said pocket into said bone.

* * * * *